United States Patent [19]

Knowles et al.

[11] 4,005,127

[45] Jan. 25, 1977

[54] L-DOPA PROCESS AND INTERMEDIATES

[75] Inventors: William S. Knowles, St. Louis;
Milton J. Sabacky, Ballwin; Billy D. Vineyard, Creve Coeur, all of Mo.

[73] Assignee: Monsanto Company, St. Louis, Mo.

[22] Filed: Aug. 6, 1975

[21] Appl. No.: 602,484

Related U.S. Application Data

[63] Continuation of Ser. No. 122,185, March 8, 1971, abandoned.

[52] U.S. Cl. .................. 260/479 R; 260/307 A; 260/519; 260/606.5 P; 260/934
[51] Int. Cl.[2] ................................ C07C 103/27
[58] Field of Search .................. 260/479 R, 519

[56] References Cited
UNITED STATES PATENTS 3,734,952    5/1973    Krubiner ................ 260/501.1

OTHER PUBLICATIONS

Horner et al. Angew. Chem. 7, (1968) Int. Ed.

Knowley et al. Chem. Comm. 1146 (1968).

*Primary Examiner*—Robert Gerstl
*Attorney, Agent, or Firm*—Howard C. Stanley; J. E. Maurer; Neal E. Willis

[57] ABSTRACT

A process for the preparation of 3-(3,4-dihydroxyphenyl)-L-alanine (L-DOPA) wherein α-acetamido-4-hydroxy-3-alkoxy-cinnamic acid acetate is subjected to catalytic asymmetric hydrogenation to yield an optically active mixture N-acetyl-3-(4-hydroxy-3-alkoxyphenyl)-alanine acetate, with the L enantiomorph being present in a major amount and the D enantiomorph being present in a minor amount, from which N-acetyl-3-(4-hydroxy-3-alkoxyphenyl)-L-alanine acetate can be easily recovered and is then converted to L-DOPA.

Novel precursors for L-DOPA are prepared in the process of this invention.

13 Claims, No Drawings

L-DOPA PROCESS AND INTERMEDIATES

This is a continuation, of application Ser. No. 122,185, filed Mar. 8, 1971, now abandoned.

This invention relates to a process for the preparation of 3-(3,4-dihydroxyphenyl)-L-alanine (L-DOPA).

L-DOPA is well known for its usefulness in treating the symptoms of Parkinson's disease.

L-DOPA has been obtained by extraction from the velvet bean. It has also been produced by chemical synthesis. The chemical synthesis route has heretofore involved the formation of a racemic mixture of chemical precursors of DOPA or of DOPA itself which mixture must then be resolved to obtain the desired L enantiomorph. These methods of production of L-DOPA have been found to be excessively complicated and expensive resulting in high production costs.

It is the primary object of this invention to provide a novel synthetic process for the preparation of L-DOPA.

It is a still further object of this invention to provide precursor compounds for the preparation of L-DOPA.

Further objects, aspects and advantages of this invention will be apparent from the description which follows.

Briefly, this invention provides a process for the preparation of L-DOPA by a synthetic chemical process utilizing commercially available compounds. Some of the precursor compounds formed during this synthetic process are new and valuable compounds useful in the synthesis of L-DOPA.

Synthesis of L-DOPA, according to this invention, can proceed in the following sequence of reactions:

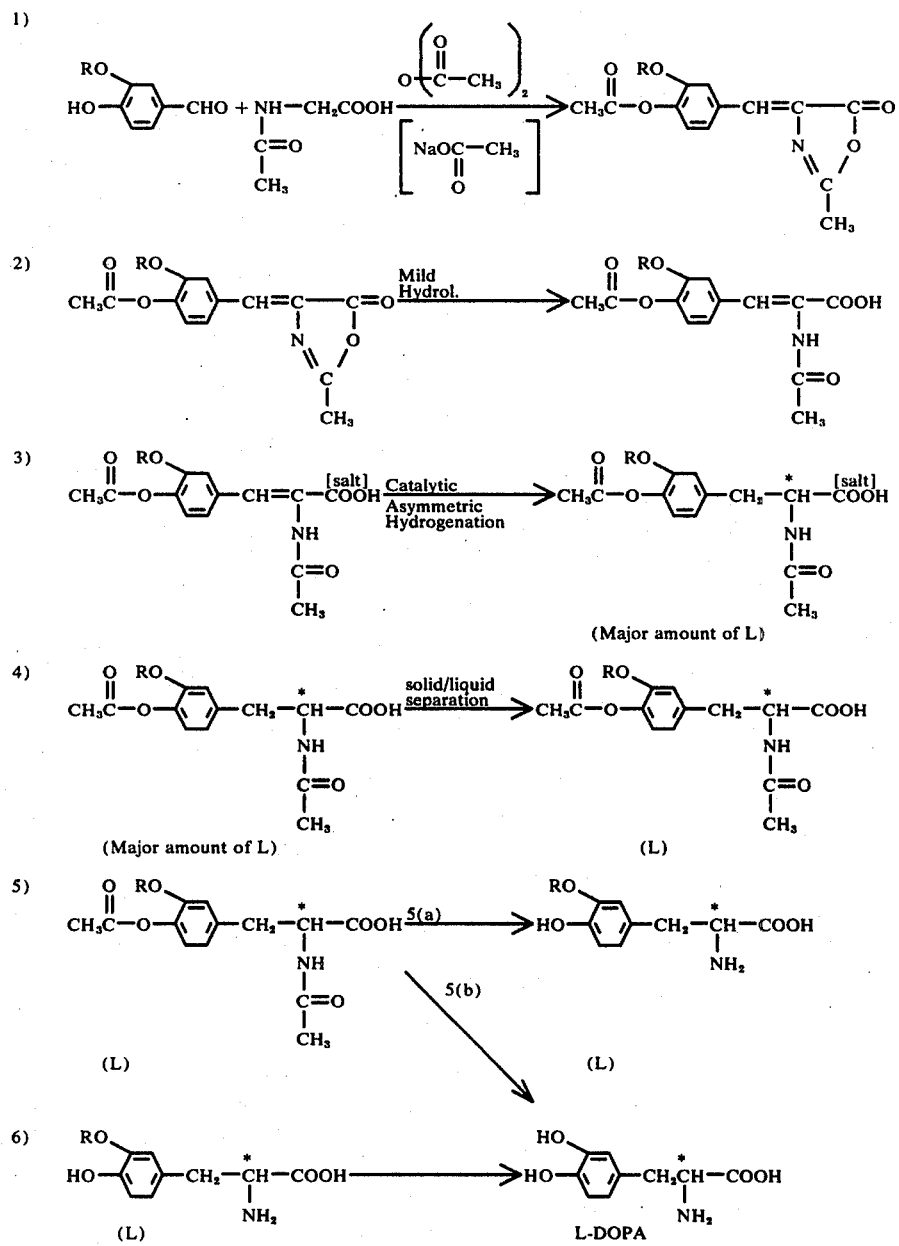

*Denotes the asymmetric carbon atom

In the above equations, R represents an alkyl group of from 1 to 3 carbon atoms.

As shown in equation 1 the starting reactants are 3-alkoxy-4-hydroxybenzaldehyde and acetylglycine reacted with acetic anhydride to form 2-methyl-4-(3'-alkoxy-4'-acetoxybenzal)-5-oxazolone. Alternately and preferably, the reaction can be carried out in the presence of sodium acetate. This reaction is known in the art as the Erlenmeyer azlactone synthesis wherein the aldehyde is condensed with an acylglycine in the presence of acetic anhydride (and usually sodium acetate). Shaw, McMillan, and Armstrong, Journal of Organic Chemistry 23,27 [1958]).

The resulting 2-methyl-4-(3'-alkoxy-4'-acetoxybenzal)-5-oxazolone is then subjected to mild hydrolysis (equation 2) to obtain α-acetamido-4-hydroxy-3-alkoxy-cinnamic acid acetate. It is critical, in carrying the process of this invention, that the hydrolysis of the azlactone be conducted in such a fashion so as to avoid the removal of the acetyl group in the 4-position on the benzal group. It has been found that the resulting compound affords an easy recovery of the desired L-enantiomorph in subsequent steps. The mild hydrolysis can be carried out, for instance, by heating the azlactone at reflux for several hours in a water-acetone solution to yield the α-acetamido-4-hydroxy-3-alkoxy-cinnamic acid acetate. It should be noted that the α-acetamido-4-hydroxy-3-alkoxy-cinnamic acid acetate can be prepared by methods other than by the Erlenmeyer azlactone synthesis such as, for instance, the acetylation of α-acetamido-4-hydroxy-3-alkoxy-cinnamic acid. It should be understood, therefore, that the process of the present invention is not limited to the use of α-acetamido-4-hydroxy-3-alkoxy-cinnamic acid acetate prepared by mild hydrolysis of an azlactone although this is a preferred method of preparing such compounds. The advantages obtained with such compounds are obtained due primarily to their usefulness in the catalytic asymmetric hydrogenation as hereinafter described and the extremely easy recovery of the resulting N-acetyl-3-(4-hydroxy-3-alkoxyphenyl)-L-alanine acetate.

α-acetamido-4-hydroxy-3-alkoxy-cinnamic acid acetate is then subjected to catalytic asymmetric hydrogenation (equation 3), as hereinafter described, resulting in the compound N-acetyl-3-(4-hydroxy-3-alkoxyphenyl)-alanine acetate. This compound is present as the two enantiomorphs, L and D; the L enantiomorph being present in a major amount and the D enantiomorph being present in a minor amount.

The above hydrogenation can be carried out, preferably, in the presence of a base. It should be noted that the α-acetamido-4-hydroxy-3-alkoxy-cinnamic acid acetate can be hydrogenated in the form of a salt or as the acid per se.

The resulting product is then subjected to crystallization procedures (equation 4) and an extremely large and unexpected proportion of the L enantiomorph can be crystallized and can be readily separated from the reaction mass. It was unexpectedly found that the L enantiomorph can be easily recovered from the above reaction product in a large number of solvents. This is particularly important in such a process for L-DOPA. Whereas this result is readily obtained with the N-acetyl-3-(4-hydroxy-3-alkoxyphenyl)-alanine acetate it does not occur with the N-acetyl-3-(4-hydroxy-3-alkoxyphenyl)-alanine thereby showing the importance of a mild hydrolysis for the preparation of such compounds as described above. It has been found that this product that separates contains approximately 98 percent of the L enantiomorph with a small amount (approximately 2 percent) of the D enantiomorph.

The recovered L enantiomorph is then subjected to hydrolysis to remove the acetyl groups from the molecule (equation 5(a)) resulting in the formation of L-3-alkoxy-tyrosine or the L enantiomorph may be subjected to a stronger hydrolysis wherein the alkyl group is also removed from the 3-position on the phenyl resulting in the direct formation of L-DOPA (alternate equation 5(b)). The product of equation 5(a) (L-3-methoxy-tyrosine) can be subjected to further hydrolysis (equation 6) also resulting in the formation of L-DOPA.

It has previously been found that optically active 3-(3,4-dihydroxyphenyl)-alanine can be prepared by catalytic asymmetric hydrogenation wherein a β-(disubstituted phenyl)α-acetylamido-acrylic acid and/or salt is hydrogenated in the presence of a catalytic amount of a homogeneous, optically active coordination metal complex catalyst comprising a metal selected from the group consisting of rhodium, iridium, ruthenium, osmium, palladium and platinum in combination with at least one optically active phosphine or arsine ligand. These catalysts are soluble in the reaction mass and are therefore referred to as "homogeneous" catalysts. Such catalytic asymmetric hydrogenation is described in greater detail in Pat. application Ser. No. 122,116 filed Mar. 8, 1971 which is a continuation-in-part of Pat. application Ser. No. 36,471, filed May 11, 1970, now abandoned, which is a continuation-in-part of Pat. application Ser. No. 758,603, filed Sept. 9, 1968, now abandoned in favor of continuation application Ser. No. 173,620, filed Aug. 20, 1971, issued as U.S. Pat. No. 3,849,480 on Nov. 19, 1974.

It has been found that such catalysts that are prepared from soluble rhodium compounds are optically active phosphine ligands containing an o-anisyl group are particularly preferred in carrying out the catalytic asymmetric hydrogenation step of the process of this invention. In particular, the soluble rhodium compounds in combination with optically active (+) methylcyclohexyl-o-anisylphosphine provide excellent results.

It should be noted here that, although the aforementioned patent applications are directed towards providing either enantiomorph as desired, the formation of the L enantiomorph in the process of the present invention can be provided by selecting an optically active catalyst and running the hydrogenation; if the resulting optically active mixture does not contain the L enantiomorph in major amount one need merely select the phosphine ligand of the opposite rotation to realize such a result.

The following examples are given to illustrate the present invention in detail. It is to be understood that the specific details given in the examples are not to be construed as limiting the scope of the invention. In the examples "parts" by weight are used unless otherwise indicated. In the examples the percent optical purity is determined by the following equation (it being understood that the optical activities expressed as specific rotations are as measured in the same solvent):

$$\% \text{ Optical Purity} = \frac{\text{Observed Optical Activity of Mixture} \times 100}{\text{Optical Activity of Pure Enantiomorph}}$$

EXAMPLE 1

The optically active phosphines and arsines can be prepared according to the procedure of Mislow and Korpiun, J. Am. Chem. Soc. 89, 4784 (1967).

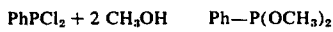

To a suitable vessel equipped with a stirring means, a temperature measuring means and a material addition means was charged 250 parts phenyldichlorophosphine, 240 parts pyridine and 495 parts hexane. The solution was cooled to about 5°–10° C. and a mixture consisting of 96 parts methanol and 27 parts hexane was added, with stirring, over a period of about 1½ hours. The resultant mixture was stirred for an additional 2½ hours at about 25° C. This reaction was conducted in an inert nitrogen atmosphere.

Pyridine hydrochloride, formed during the reaction, was filtered and the filtrate concentrated. The yellow residue was distilled, collecting a colorless fraction boiling at 95.5°–97° C./17 mm. (82 percent yield of dimethylphenylphosphonite) [Harwood and Grisley, J. Am. Chem. Soc., 82, 423 (1960)].

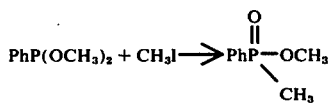

To a suitable vessel equipped with a stirring means, a temperature measuring means and a material addition means was charged 11 parts dimethylphenylphosphonite, 2.5 parts methyl iodide and 9 parts toluene. The resultant solution was slowly heated. The reaction is exothermic and the temperature increases to about 110° C., the reaction mixture is maintained at a temperature of about 100°–120° C., and an additional 185 parts dimethylphenylphosphonite slowly added. Additional amounts of methyl iodide, in about 1 part increments, are occasionally added during the phosphonite addition. The reaction mixture was maintained at about 110° C. for an additional hour following the addition of components. The reaction mixture was then distilled collecting the portion boiling at 148°–149° C./17 mm. (96 percent yield of methyl phenylmethylphosphinate). [Harwood and Grisley J. Am. Chem. Soc., 82, 423 (1960)].

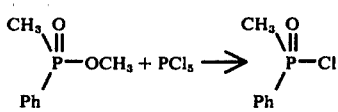

To a suitable vessel equipped with a stirring means, a condensing means, temperature measuring means and a material addition means, was charged 187 parts methyl phenylmethylphosphinate and 1600 parts carbon tetrachloride. To this mixture was added 229 parts phosphorus pentachloride in three portions of 50 parts and one portion of 79 parts. A temperature rise was observed on the addition of the first three portions. The mixture was stirred at about 60° C. for 2 hours and then the carbon tetrachloride and phosphorous oxychloride removed by distillation. The residue was distilled collecting the fraction boiling at 138°–141° C./17 mm. (95 percent yield of methylphenylphosphinic chloride).

[Methoden Der Organishen Chemie (Houben-Weyl) Vol. XII/I p. 243].

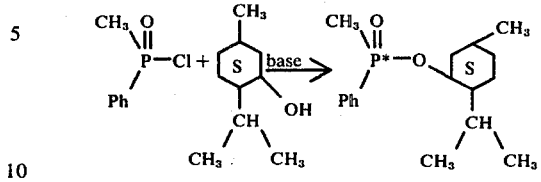

To a suitable vessel equipped with a stirring means, a condensing means, a temperature measuring means, and a material addition means, was added 78 parts l-menthol and 72 parts diethyl ether. To the resultant solution was added 119 parts of triethylamine and the resultant mixture cooled to about 0° C. To this mixture was added, with stirring 87 parts methylphenylphosphinic chloride over a period of about 1½ hours while maintaining the temperature at about 0° C. The mixture was allowed to warm to about 25° C. and then heated at reflux for about 10½ hours.

The mixture was filtered to remove the triethylamine hydrochloride and the filtrate concentrated. The filtrate, upon concentration, yielded a solid melting at 50°–65° C. which is a mixture of l-menthyl methylphenylphosphinate diastereoisomers (60% S and 40% R).

The mixture of l-menthyl methylphenylphosphinate diastereoisomers were resolved by crystallization from hexane and/or hexane-ether resulting in an S form melting at 78°–82° C. having specific rotation $[\alpha]_D^{25} = -94°$ (benzene) and an R form melting at 86°–87° C. having specific rotation $[\alpha]_D^{25} = -17°$ (benzene).

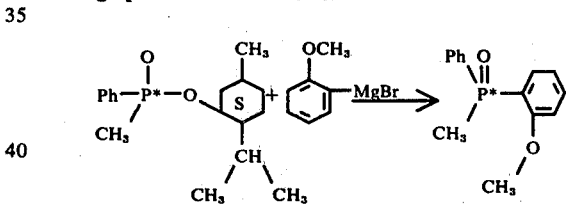

To a suitable vessel equipped with a stirring means, temperature measuring means, material addition means and a condenser means, under an inert nitrogen atmosphere was added 18.3 parts magnesium turnings, 14 parts diethyl ether and a reaction initiating amount of iodine. A small amount of o-anisylbromide was added to initiate the reaction and then a mixture consisting of 138 parts of o-bromoanisole and 400 parts diethyl ether was slowly added at a rate to maintain gentle refluxing of the reaction mixture. After completion of addition the mixture was refluxed an additional two hours.

To this mixture was added a mixture consisting of 74 parts of the R form of l-menthyl methylphenylphosphinate (the choice of S or R depends on the enantiomorph desired) and 450 parts benzene. The diethyl ether was then removed and the resultant mixture heated at 78° C. for 64 hours.

The magnesium complex reaction product was decomposed with a solution of ammonium chloride and the product extracted from the aqueous phase with benzene. After removal of the benzene the residual oil was distilled, first removing a menthol cut and finally taking over product at 180°–190° C. and 0.5 mm. pressure. The crude material was formed in 60 percent yield. Using the R isomer methylphenyl-o-anisylphosphine oxide having a specific rotation $[\alpha]_D^{25} = +27°$ (methanol) was obtained.

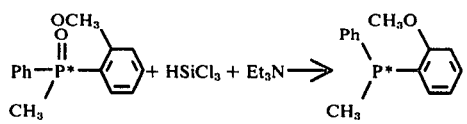

To a suitable vessel, having an inert nitrogen atmosphere, equipped with stirring means, temperature measuring means and a material addition means, was charged 16 parts of trichlorosilane and 100 parts of benzene at about 5° C. To this mixture at 4°–6° C. was added a mixture of 12 parts triethylamine and 50 parts benzene. The resultant mixture was warmed to 70° and a mixture of 7.5 parts (+) methylphenyl-o-anisylphosphine oxide in 30 parts of benzene was added. The mixture was heated to 70° for a one-hour period and then cooled to 25° C.

The silicon complex reaction product was decomposed by adding under nitrogen to 75 parts of 20 percent sodium hydroxide at 25° C. with cooling. The organic layer containing the desired phosphine is separated and a 95 percent yield of methylphenyl-o-anisylphosphine was obtained having a specific rotation $[\alpha]_D^{25} = +41°$ (methanol) when the above prepared phosphine oxide having a specific rotation $[\alpha]_D^{25} = +27°$ (methanol) was used.

EXAMPLE 2

Preparation of methylcyclohexyl-o-anisyl phosphine

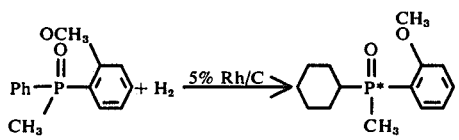

To a one liter autoclave was added 143 parts of (+) methylphenyl-o-anisylphosphine oxide and 28 parts of 5 percent rhodium on carbon and 250 parts methanol. The batch was heated to 75° C. and stirred under 800 psig. of hydrogen. When hydrogen uptake ceased, nmr analysis showed that the reaction was 75 percent complete. A further 7.0 parts of catalyst was added, the batch repressurized to 800 psig. and the batch was run to 96 percent completion.

The catalyst was filtered and the methanol removed under vacuum. The crude oil was taken up in 200 parts of dibutyl ether and cooled to 0° C. The crystals which separated were filtered and washed with hexane. There was obtained 63 parts of methylcyclohexyl-o-anisylphosphine oxide melting at 108°–110° C. having a specific rotation $[\alpha]_D^{20} = +63°$ (methanol).

The above phosphine oxide can be reduced to methylcyclohexyl-o-anisylphosphine in 95 percent yield using HSiCl$_3$ and triethylamine exactly as described above for methylphenyl-o-anisylphosphine. The resulting methylcyclohexyl-o-anisylphosphine is a liquid having a specific rotation $[\alpha]_D^{20} = +98.5°$ (methanol).

EXAMPLE 3

Into a suitable reaction vessel was charged 300 grams (2.9 moles) of acetic anhydride, 10 grams (0.25 moles) sodium hydroxide and 152 grams (1.0 moles) vanillin. The resulting mass is brought to a temperature of about 90° to 100° C. in a solution that is made by heating at 100° C. one mole of glycine and one mole of acetic anhydride is added over a period of 1 hour (0.5 mole of acetylglycine). The reaction mass is held at about 90° to 95° C. for about 2 hours and then cooled to 50° C. to crystallize out 2-methyl-4-(3'-methoxy-4'-acetoxybenzal)-5-oxazolone; 124 grams (0.42 mole) are recovered. This material is washed with cold acetic acid which may be returned to the reaction.

100 Grams of the resulting azlactone is slurried in a solution of 100 grams of water and 300 grams of acetone. The slurry is heated to reflux (approximately 65° C. and held there for about 3 to 4 hours. The acetone is then distilled until crystallization begins (about 73° to 75° C.) and is then cooled to room temperature with the solid material being filtered therefrom. The acetone removed can be recycled. Approximately 90 to 95 percent yield by weight of α-acetamido-4-hydroxy-3-methoxy-cinnamic acid acetate is obtained.

A one liter autoclave was charged with 100 grams (0.341 mole) of α-acetamido-4-hydroxy-3-methoxy-cinnamic acid acetate, 254 milliliters of methanol, 170 milliliters of water and 13.7 (0.341 mole) sodium hydroxide. The slurry obtained was brought to about 25° C. and 40 psig. hydrogen pressure and a catalyst solution in 6 milliliters of benzene that was made from 0.025 gram (0.115 milli-equivalents) of rhodium 1,5-hexadiene chloride [Rh-(1,5-hexadiene)Cl]$_2$ (J. Am. Chem. Soc. 86, 217 (1964)), and 0.058 gram (0.250 milli-equivalents) (+) methylphenyl-o-anisylphosphine (while preventing intrusion of air) is added. (The catalyst charge is equivalent to 0.0118 gram rhodium metal.) Hydrogen is absorbed immediately and is complete in 8 hours, giving the compound, N-acetyl-3-(4-hydroxy-3-methoxyphenyl)-alanine acetate, with 80 percent of such compound being present as the L enantiomorph and 20 percent being present as a D enantiomorph.

After the reaction the methanol is stripped under the vacuum up to about 65° C. Concentrated hydrochloric is added (40 grams) and the L enantiomorph crystallizes out while the remaining solution contains an equal proportion of D and L enantiomorphs. If one wishes to recover further L enantiomorph one can go through a conventionally known resolution step.

To a solution of 122 grams (1.50 moles) of hydrogen bromide in 128 grams of water (47%) is added 89.0 grams (0.30 mole) N-acetyl-3-(4-hydroxy-3-methoxyphenyl)-L-alanine acetate and the mass is refluxed at about 105° to 110° C. for three hours, during which time 28 grams (0.30 mole) of bromomethane is evolved. At the completion of the reaction the reaction mass is cooled to 25° to 30° C. and neutralized to pH 3 with 48 grams of sodium hydroxide. L-DOPA crystallizes out and is recovered by filtration and washing with cold water.

If necessary, L-DOPA can be recrystallized from hot water, for instance, in a 3 to 4 percent solution to give a pharmaceutical grade product.

EXAMPLE 4

An autoclave was charged with 25.0 g. (0.085 mole) of α-acetamido-4-hydroxy-3-methoxy-cinnamic acid acetate, 300 ml. of methanol and 0.36 ml. of 50 percent NaOH. The autoclave was pressurized with a 50/50 mixture of N$_2$ and H$_2$ to 35 psig.

A catalyst solution was prepared by dissolving 0.0050 g. (0.023 meq.) of rhodium 1,5-hexadiene chloride, [Rh(1,5 hexadiene)Cl]$_2$, (J. Am. Chem. Soc. 86, 217 (1964)), in 0.5 ml. of benzene and adding, under N$_2$ 0.051 meq. of (+) methylcyclohexyl-o-anisylphosphine (optical purity = about 90 percent) in 2.4 ml. of benzene. Hydrogen was bubbled through this solution for ten minutes. The catalyst solution was then added to the autoclave. The hydrogenation was carried out at 60° C. and was complete in 4 hours.

The product obtained by evaporation of the solvent has a specific rotation $[\alpha]_D^{25} = +38.2°$ (Na salt in water). Pure N-acetyl-3-(4-hydroxy-3-methoxyphenyl)-L-alanine acetate, also as a sodium salt in water, had a specific rotation $[\alpha]_D^{25} = +54.0°$. Thus, the optical purity of the sample was 70.7 percent or better than a 85/15 ratio of the L/D enantiomorphs.

The N-acetyl-3-(4-hydroxy-3-methoxyphenyl)-L-alanine acetate can be easily recovered by crystallization and converted to L-DOPA as in Example 3.

EXAMPLE 5

Asymmetric hydrogenation of α-acetamido-4-hydroxy-3-methoxy-cinnamic acid acetate To a hydrogenation apparatus, as in Example 4, was added 596 parts of methanol, 0.9 parts of triethylamine and 149 parts of α-acetamido-4-hydroxy-3-methoxy-cinnamic acid acetate. The slurry was heated to 50° and thoroughly purged to remove all traces of oxygen and finally adjusted to 50° C. and 40 psig. of hydrogen.

A catalyst solution made by dissolving 0.036 parts of rhodium 1,5-cyclooctadiene chloride in 1.9 parts of benzene followed by 0.075 parts of (+) methylcyclohexyl-o-anisylphosphine in 1 part of methanol was added and the mixture treated with hydrogen for 5 minutes. The resulting clear solution was then forced into the hydrogenation apparatus under hydrogen pressure. Hydrogenation begins immediately and is complete in about 2 hours. Assay of the reaction mixture shows the optical purity to be 72 percent, corresponding to an 86/14 L/D mixture.

One hundred parts of pure N-acetyl-3-(4-hydroxy-3-methoxyphenyl)-L-alanine acetate can be obtained by distilling off 422 parts of methanol and crystallizing followed by a washing of the resulting crystals with methanol. The product melts at 180° C. and has a specific rotation $[\alpha]_D^{20} = +40.5°$ (methanol).

Using a similar procedure with (−) methylcyclohexyl-o-anisylphosphine there was obtained the D analog in 65 percent optical purity. Thus, by proper choice of phosphine either enantiomorph can be obtained in major amounts.

While the illustrative embodiments of the invention have been described hereinbefore with particularity it will be understood that various other modifications will be apparent to and can be readily made by those skilled in the art without departing from the scope and spirit of the invention. Accordingly, it is not intended that the scope of the claims appended hereto be limited to the examples and descriptions set forth herein but rather that the claims be construed as encompassing all the features of patentable novelty which reside in the present invention including all features which would be treated as equivalents thereof by those skilled in the arts to which the invention pertains.

The embodiments of this invention in which a particular property or privilege is claimed are defined as follows:

1. A process comprising catalytically asymmetrically hydrogenating α-acetamido-4-hydroxy-3-alkoxy-cinnamic acid acetate, in the presence of a homogeneous, optically active coordination complex of a metal selected from the group consisting of rhodium, iridium, ruthenium, osmium, palladium and platinum in combination with at least one optically active phosphine or arsine ligand to form N-acetyl-3-(4-hydroxy-3-alkoxyphenyl)-L-alanine acetate in a major amount and N-acetyl-3-(4-hydroxy-3-alkoxyphenyl)-D-alanine acetate in a minor amount and recovering a portion of the N-acetyl-3-(4-hydroxy-3-alkoxyphenyl)-L-alanine acetate by crystallization and hydrolyzing the recovered N-acetyl-3-(4-hydroxy-3-alkoxyphenyl)-L-alanine acetate to 3-(3,4-dihydroxyphenyl)-L-alanine; provided that said α-acetamido-4-hydroxy-3-alkoxy-cinnamic acid acetate, N-acetyl-3-(4-hydroxy-3-alkoxyphenyl)-L-alanine acetate and N-acetyl-3-(4-hydroxy-3-alkoxyphenyl)-D-alanine acetate may be present as the acid, a salt formed with a base or mixtures of the acid and a salt formed with a base.

2. A process according to claim 1 wherein the α-acetamido-4-hydroxy-3-alkoxy-cinnamic acid acetate is prepared by mild hydrolysis of 2-methyl-4-(3'-alkoxy-4'-acetoxybenzal)-5-oxazolone.

3. A process according to claim 1 wherein the metal is rhodium.

4. A process according to claim 1 wherein the homogeneous, optically active coordination complex is prepared from a soluble rhodium compound and an optically active phosphine containing an o-anisyl group.

5. A process according to claim 4 wherein the phosphine is (+) methylphenyl-o-anisylphosphine.

6. A process according to claim 4 wherein the phosphine is (+) methylcyclohexyl-o-anisylphosphine.

7. A process according to claim 3 wherein the optically active ligand is a phosphine.

8. A process comprising forming a solution containing N-acetyl-3-(4-hydroxy-3-methoxyphenyl)-L-alanine acetate in a major amount and N-acetyl-3-(4-hydroxy-3-methoxyphenyl)-D-alanine acetate in a minor amount and recovering a portion of the N-acetyl-3-(4-hydroxy-3-methoxyphenyl)-L-alanine acetate by crystallization and hyrolyzing the recovered N-acetyl-3-(4-hydroxy-3-methoxyphenyl)-L-alanine acetate to 3-(3,4-dihydroxyphenyl)-L-alanine; provided that said N-acetyl-3-(4-hydroxy-3-methoxyphenyl)-L-alanine acetate and N-acetyl-3-(4-hydroxy-3-methoxyphenyl)-D-alanine acetate may be present as the acid, a salt formed with a base or mixtures of the acid and a salt formed with a base.

9. A composition which is a product of the process comprising catalytically asymmetrically hydrogenating α-acetamido-4-hydroxy-3-alkoxy-cinnamic acid acetate, in the presence of a homogeneous, optically active coordination complex of a metal selected from the group consisting of rhodium, iridium, ruthenium, osmium, palladium and platinum in combination with at least one optically active phosphine or arsine ligand to form N-acetyl-3-(4-hydroxy-3-alkoxyphenyl)-L-alanine acetate in a major amount and N-acetyl-3-(4-hydroxy-3-alkoxyphenyl)-D-alanine in a minor amount; provided that said α-acetamido-4-hydroxy-3-alkoxy-cinnamic acid acetate, N-acetyl-3-(4-hydroxy-3-alkoxyphenyl)-L-alanine acetate and N-acetyl-3-(4- hydroxy-3-alkoxyphenyl)-D-alanine acetate may be present as the acid, a salt formed with a base or mixtures of the acid and a salt formed with a base and that the alkoxy has from 1 to 3 carbon atoms.

10. The composition of claim 9 wherein the alkoxy is methoxy.

11. A compound represented by the structural formula

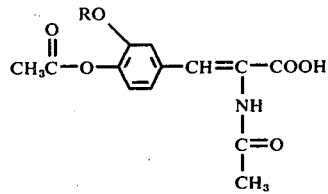

and its salts formed with a base, wherein, R is alkyl of from 1 to 3 carbon atoms.

12. A compound of claim 11 wherein R is methyl.

13. α-acetamido-4-hydroxy-3-methoxy-cinnamic acid acetate.

* * * * *